United States Patent [19]

Barker

[11] 4,075,884
[45] Feb. 28, 1978

[54] FRACTURE SPECIMEN LOADING MACHINE

[75] Inventor: Lynn Marshall Barker, Salt Lake City, Utah

[73] Assignee: Terra Tek, Inc., Salt Lake City, Utah

[21] Appl. No.: 768,193

[22] Filed: Feb. 14, 1977

[51] Int. Cl.² ............................................. G01N 3/36
[52] U.S. Cl. ..................................................... 73/91
[58] Field of Search ...................... 73/38, 96, 88 E, 97, 73/88 R, 91

[56] References Cited

U.S. PATENT DOCUMENTS

| | | | |
|---|---|---|---|
| 322,800 | 7/1885 | Cummings | 73/97 |
| 2,321,875 | 6/1943 | Temple | 73/97 |
| 2,957,341 | 10/1960 | Menard | 73/88 E UX |
| 3,473,386 | 10/1969 | Nielsen, Jr. et al. | 73/398 AR |

Primary Examiner—Jerry W. Myracle
Attorney, Agent, or Firm—M. Reid Russell

[57] ABSTRACT

A machine that can be used for loading of a slotted specimen for measuring the fracture toughness, fatigue crack growth resistance, or stress corrosion crack growth resistance of that specimen, the machine having a pressure bag maintained in a frame, which pressure bag can be installed within the slotted portion of the specimen and expanded to produce a desired specimen loading, the machine preferably involving a load pressure sensing device, can optionally include an arrangement for sensing volume enlargement of the specimen slot, and can also include a movable frame portion that expands with the pressure bag during inflation to discourage crimping of that pressure bag during specimen loading.

21 Claims, 9 Drawing Figures

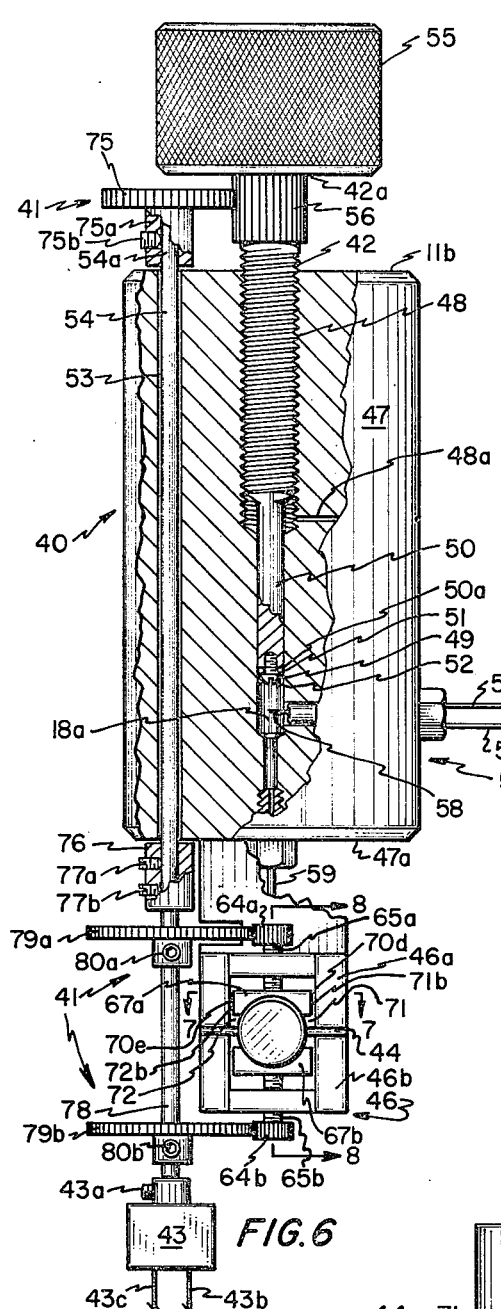
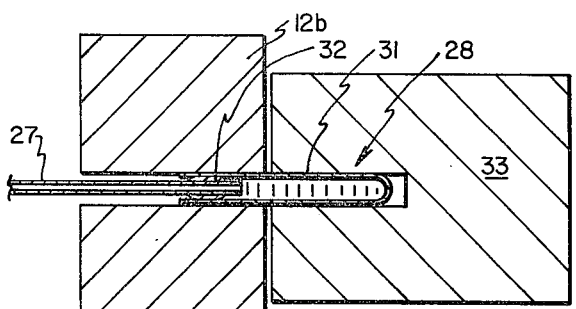
FIG. 5a
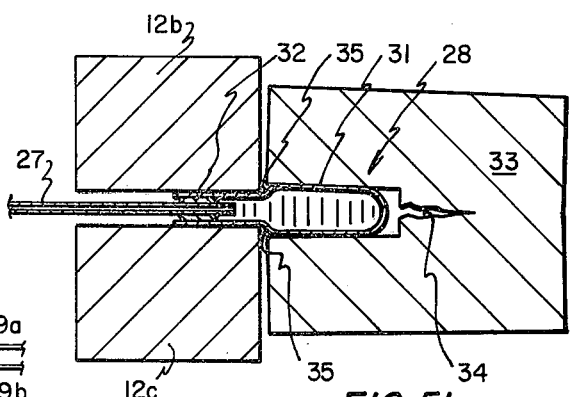
FIG. 5b
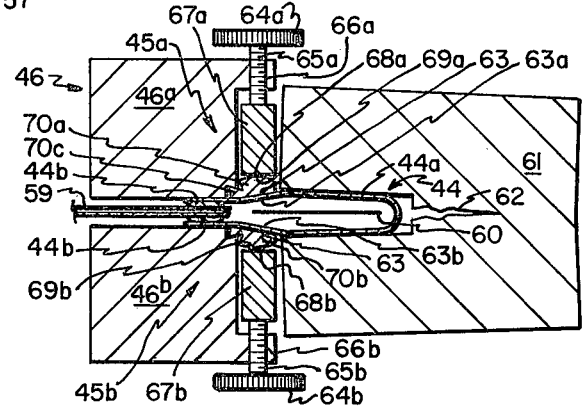
FIG. 8
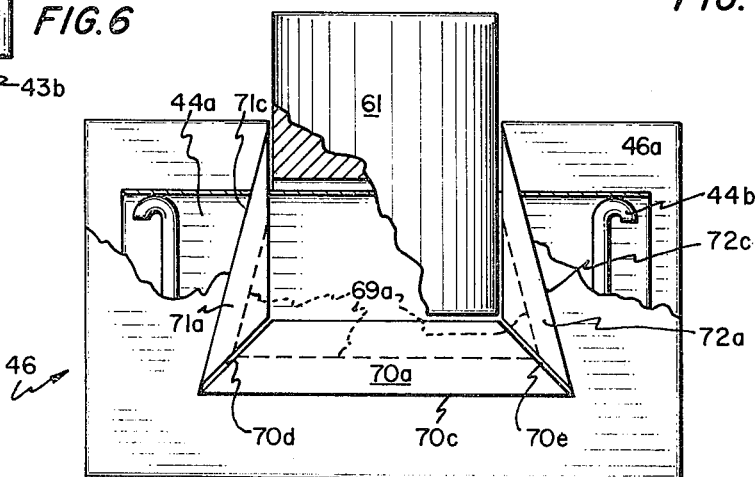
FIG. 7

FRACTURE SPECIMEN LOADING MACHINE

BRIEF DESCRIPTION OF THE INVENTION

1. Field of the Invention

This invention relates to the discipline of fracture mechanics in which test machines are used for loading of slotted specimens to induce cracking and/or fracture thereof.

2. Prior Art

The testing of materials for fracture toughness, fatigue crack growth resistance, and stress corrosion crack growth resistance is most often done with specimens containing a machined slot from which slot crack growth initiates. Such tests all involve an appropriate specimen loading sequence, whence the loading applied to the specimen tends to increase the machined slot width.

Materials testing machines capable of providing such loading have long been known and are in common use. Such machines often involve arms that lock to parts of such specimen and, when energized, move apart, widening the specimen slot. Such machines can be "soft", applying a constant load to the specimen that continues through specimen cracking and fracture, or can be "stiff", maintaining, ideally, a constant specimen slot opening by including a locking of the jaws after each increment of load increase. An example of a soft machine configuration could be a specimen hung between wires with a bucket attached to said wire below the specimen. Into such bucket water is poured until the sample fractures. A stiff machine could involve jaws attached to the specimen and moved apart by gear or hydraulic means that includes a locking feature to prohibit jaw movement when a drop in load force occurs, as when the sample begins to fracture.

Such soft and stiff machines, it should be understood, could, of course, be used in testing slotted and unslotted specimens, whereas the machine of the present invention, as mentioned hereinabove, operates only on slotted specimens, loading such specimens by inflation of a pressure bag installed within that slot.

Heretofore, to provide a device having stiff machine characteristics has necessitated a large machine utilizing heavy construction to minimize the elastic response of the machine when a rapid load change occurs. The present invention, by limiting fluid volume changes in the system provides the required stiff characteristics in a small portable device that costs far less than, but has equal or better reliability and accuracy than does a larger machine that operates a conventional jaw arrangement. Loading of the machine of the present invention involves hydraulic expansion of a pressure bag that is capable of freely expanding and contracting and can be continuous or cyclic.

Within the knowledge of the inventor, the fracture specimen loading machine of the present invention is unlike any machine known or in use in its construction, its operation and its test performing capabilities.

SUMMARY OF THE INVENTION

It is a principal object of the present invention to provide a compact machine for loading of a slotted fracture test specimen.

Another object is to provide a fracture specimen loading machine incorporating, as the load generating portion, a pressure bag whereon the slotted portion of the specimen is fitted, and into which pressure bag hydraulic fluid is introduced to expand the pressure bag and load the specimen, the machine to include a pressure sensor for measuring the hydraulic fluid pressure within the pressure bag, which fluid pressure constitutes the load on the specimen.

Another object is to provide a fracture specimen loading machine utilizing, as the load generating portion, a pressure bag capable of being pressurized and unpressurized, expanding and contracting so as to cyclically load and unload a slotted specimen installed over the pressure bag.

Another object is to provide a fracture specimen loading machine for use with slotted specimens arranged such that alignment of the specimen on a load generating portion thereof is not critical to specimen loading.

Another object is to provide a fracture specimen loading machine that functions as a stiff machine providing for controlled displacement loading of the specimen.

Still another object is to provide a fracture specimen loading machine utilizing a pressure bag mounted in a frame as the load generating portion of the machine, that frame incorporating movable parts therewith that will expand with the pressure bag to prohibit or limit crimping of the pressure bag during expansion thereof.

Still another object is to provide a fracture specimen loading machine capable of being manufactured as a small, yet precision device.

Still another object is to provide a portable fracture specimen loading machine that is efficient and reliable and that is simple to operate.

The principal features of the present invention in a fracture specimen loading machine include a housing wherein a pressure chamber is formed, which chamber preferably receives a piston moved therein as by an external power source, so as to generate or abate a hydraulic pressure in that chamber. Fluid under pressure passes from the chamber through a single or plurality of high pressure inflation tubes into a pressure bag. The pressure bag is preferably formed from a sheet of thin gauge metal, such as stainless steel, that is folded into an envelope over a gasket, preferably formed of copper or a like metal, through which gasket the single or plurality of inflation tubes are installed. The envelope and gasket are pressed together in a frame, effecting a plastic flow of the gasket, providing thereby a seal that is a number of times stronger than is the pressure that will be exerted by a fluid forced therein, that pressure causing the pressure bag to inflate to load a specimen, as will be described.

The frame holding the pressure bag is secured, as by bolts or the like, to the housing and is arranged such that the pressure bag is maintained in a U-shaped portion thereof. The U-shaped frame portion is just sufficient to allow for passage of a slotted specimen therein, the specimen slot traveling over the pressure bag, which pressure bag is then inflated to load the sample. In such loading, the sides of the frame prohibit inflation of that pressure bag around the specimen sides.

Preferably incorporated within, or connected to the housing pressure chamber is a pressure sensing device for measuring the pressure of the fluid therein, which pressure is also the fluid pressure within the pressure bag. Such pressure sensing device can be a pressure transducer having a diaphragm or like arrangement whose deflection senses pressure changes, or, should it be desired to limit fluid flow as much as possible to only the pressure bag so as to stiffen the operations of the machine of the invention, a strain gauge or a piezoresistive type of pressure transducer could be installed in the housing pressure chamber or in the pressure bag itself.

As nearly any fluid used as the hydraulic medium in the machine is more compressible than the metal of the pressure chamber of the pressure bag, limiting the volume of that fluid used in the machine further stiffens the operation of the machine. Therefore, as desired, an insert, preferably of metal, can be installed in said pressure bag, taking up part of the volume therein.

To prohibit crimping of the pressure bag at the bottom of the U-shaped portion of the frame as the specimen is loaded it may be desirable to appropriately hinge a portion or portions of that frame to open around that U-shaped portion as the pressure bag is expanded and the specimen slot widens. Such frame opening can be mechanically controlled as by an appropriate gear train operated by turning the piston into and out of the pressure chamber. This gear train for opening appropriate portions of the frame can also be connected to a potientometer, or the like, calibrated to compute fluid volume within the pressure bag, which fluid volume can be used to determine specimen slot width.

Further objects and features of the present invention will become apparent from the following detailed description, taken together with the accompanying drawings.

THE DRAWINGS

FIG. 1, is a profile perspective view taken from the front and to one side of a first embodiment of the fracture specimen loading machine of the present invention;

FIG. 2, a sectional view of the fracture specimen loading machine of FIG. 1 taken along the line 2—2 therein;

FIG. 3, a top profile view of a pressure bag of the present invention shown as a sheet of material arranged for folding over a U-shaped gasket, through the bottom of which gasket is shown installed an inflation tube;

FIG. 4, a top profile view of the pressure bag sheet of FIG. 3 shown folded over the U-shaped gasket;

FIG. 5(a), an expanded sectional view of the frame and pressure bag of FIG. 2, taken along the line 5—5 therein, showing also a profile sectional view of a slotted specimen with the slot thereof installed over that pressure bag, which pressure bag is shown in a deflated state;

FIG. 5(b), a view like that of FIG. 5(a) showing the pressure bag expanded and the specimen partially fractured;

FIG. 6, a profile sectional view of a second embodiment of a fracture specimen loading machine showing portions of the housing thereof broken away to expose the interior thereof;

FIG. 7, an expanded sectional view of jaw and pressure bag portions of the fracture specimen loading machine of FIG. 6, taken along the lines 7—7 thereof, showing portions of the jaw and sample broken away and showing movable portions of that frame; and FIG. 8, a view like that of FIGS. 5(a) and 5(b) taken along the line 8—8 of FIG. 6, only showing, additional to the pressure bag with slotted specimen thereover, the frame, expandable portions of that frame with the pressure bag shown as containing a plate insert and is expanded to fracture the specimen.

DETAILED DESCRIPTION

Figure 1:
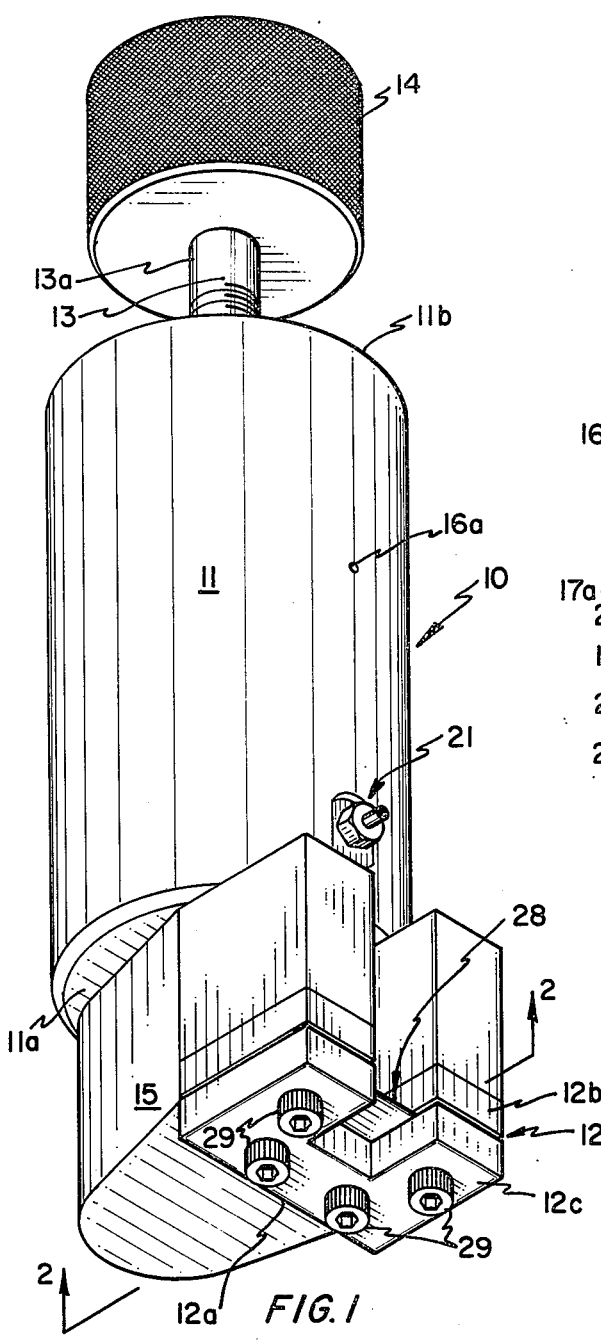

Referring now to the drawings:

In FIG. 1 is shown a first embodiment of a fracture specimen loading machine 10 of the present invention, hereinafter referred to as machine. Shown therein the machine 10 consists of a housing 11 connecting, at its one end 11a to a frame 12 and having a threaded rod 13 turned into its other end 11b. The threaded rod 13 is shown having a handle 14 secured across its external end 13a, which handle 14 is shown to be cylindrical and is appropriately cross-hatched to provide a non-slip gripping surface for manual turning by an operator, not shown. Turning handle 14, as will be explained later herein, creates a hydraulic pressure buildup to operate machine 10. While handle 14 is a preferred arrangement for appropriately turning threaded rod 13, obviously other arrangements could be used to manually or mechanically turn the rod. A cover 15 is provided over a rear face 12a of a frame 12 and end 11a of housing 11.

Figure 2:
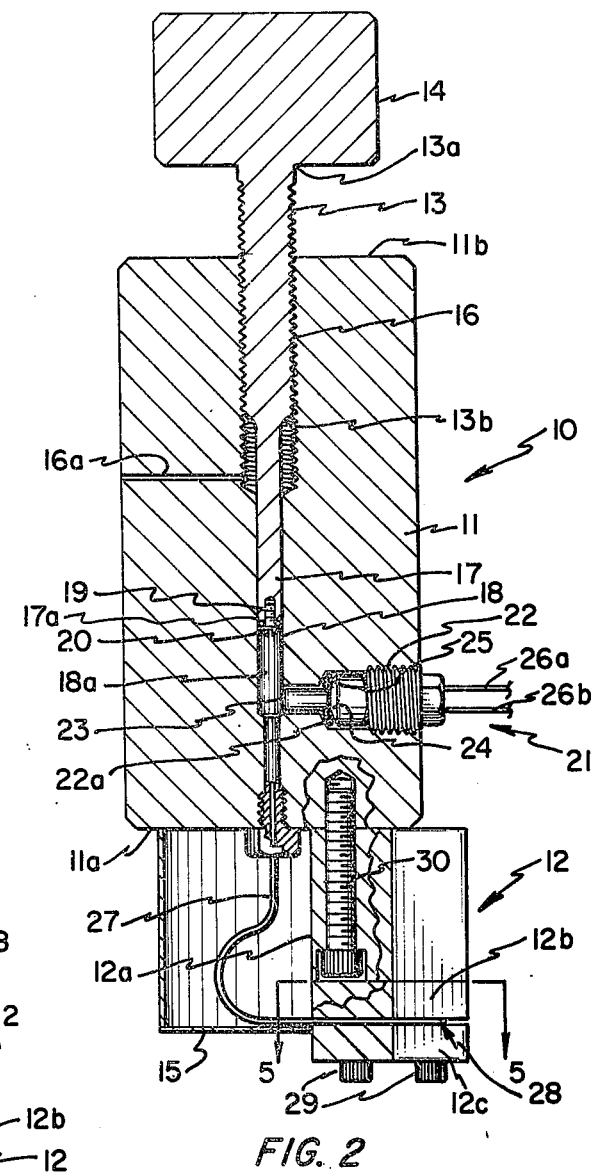

Referring to FIG. 2, which figure is a profile sectional view of the machine 10. Shown therein, the housing 11 has a bore 16 formed longitudinally therein that is threaded at the top thereof, in the threaded portion of which bore 16 the threaded rod 13 is turned. Turning of handle 14 causes rod 13 to be screwed into or out of bore 16 moving thereby a piston 17 that is secured to rod end 13b within a pressure chamber 18 formed in housing 11. A port 16a is formed in housing 11 for venting the area of threaded bore 16 above piston 17 to preclude a pressure buildup therein. The piston 17 at its end 17a opposite to its connection to rod end 13b has mounted thereto a gasket or O-ring seal 19 by screw 20. Turning screw 20 expands the outer circumference of the O-ring seal 19 into sealing engagement with the wall of pressure chamber 18 prohibiting fluid bypass into bore 16. O-ring seal 19, as will be explained later herein relating to desirable stiff machine operations, is preferably formed from material that has minimal deformation when subjected to pressure and should, of course, be as thin as possible minimizing its surface area subjected to pressure deformation.

Shown in FIG. 2, a pressure transducer 21 is maintained within a threaded lateral bore 22 formed in the side of housing 11. In this embodiment the pressure transducer 21 is shown to be of a type involving a strain-gauged diaphram 23 that is arranged to flex in response to fluid pressure exerted thereon by a fluid 18a within the pressure chamber 18. A sealing ring 25 is shown compressed between a tapered portion 22a of the threaded lateral bore 22 and a tapered base 24 of the sensor body portion. Obviously, as pressure changes in the pressure chamber 18 cause a deflection of the strain-gauged diaphram 23, a resultant fluid volume change, though slight, occurs within the pressure chamber 18. Such volume changes, as covered hereinabove, and as will be elaborated on later herein, are not desirable as they tend to "soften" machine 10 functioning.

Therefore, while the example of the pressure transducer 21 shown in FIG. 2 can be used in machine 10, other types of sensing devices, such as a piezoresistive wire may be more desirable to provide optimum stiff machine operations. With such a piezoresistive wire installed in pressure chamber 18 changes in resistance reflecting changes in pressure can be measured across wires 26a and 26b and shown on an appropriate meter, recording device, or the like, not shown.

Shown in FIG. 2, fluid under pressure passes from the pressure chamber 18, through a pressure bag inflation tube 27 that is preferably a small stainless steel tube, hereinafter referred to as inflation tube, and into a pressure bag 28. The pressure bag 28, as shown in FIGS. 1 and 2, is sandwiched between upper and lower U-shaped frame sections 12b and 12c, with the pressure bag occupying part of the open area within the U-shaped sections. Bolts 29 maintain the frame sections 12b and 12c together and, as shown in FIG. 2, bolts 30 secure the frame 12 to the housing end 11a, aligning the pressure bag 28 at a normal angle thereto, which normal angle configuration is, however, not a factor in the operations of the machine 10.

Figure 3:
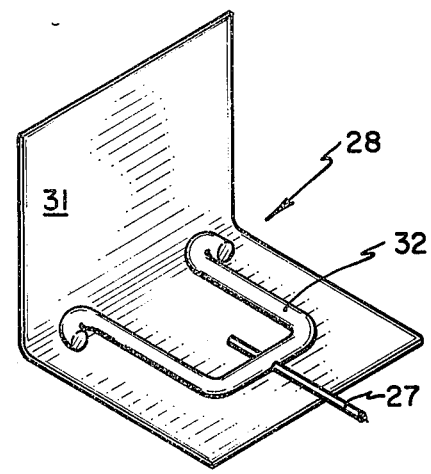

Pressure bag 28 is shown in FIG. 3 being formed from a flat sheet of metal 31, preferably a stainless steel, or the like, that is folded in half over a horseshoe shaped gasket 32, that is preferably fabricated from copper, or a like metal that is capable of a plastic flow when it is compressed between the surfaces of the sheet of metal 31, effecting a pressure seal therewith. Shown also in FIG. 3, the inflation tube 27 is fitted through the bottom of the gasket 32 to pass fluid, under pressure, into the formed pressure bag 28. While only one inflation tube is shown in FIG. 3, it should be obvious that a number of such tubes could be so arranged, each connected to receive fluid from pressure chamber 18. Utilization of a plurality of such inflation tubes minimizes the likelihood of malfunctioning of the machine due to a stoppage in the inflation tube as by a piece of material being lodged therein and the response of the machine is improved as the volume of the fluid flow is increased with each inflation tube used. Stoppage due to a piece of material lodging in an inflation tube is possible because the inflation tube in this embodiment is very small, from 0.009 inches to 0.011 inches in outside diameter and from 0.002 inches to 0.003 inches in inside diameter, and therefore utilizing a plurality of inflation tubes may be desirable though, of course, only one such tube is required.

Figure 4:
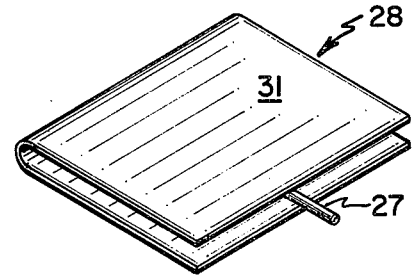

Shown in FIG. 4, the sheet of metal 31 is folded into an envelope for installation, as shown in FIGS. 1 and 2 between the frame sections 12b and 12c as bolts 29 are tightened, appropriately, compressing the gasket 32 to seal the envelope formed by the sheet of metal 31 into the pressure bag 28. In FIG. 5(a), pressure bag 28 is shown with a slotted specimen 33 fitted thereover.

FIG. 5(a) shows the pressure bag 28 in its relaxed state. By appropriately turning the rod handle 14, piston 17 is moved into pressure chamber 18, forcing fluid therein, under pressure, through the inflation tube 27, and into the pressure bag 28. The pressure bag 28 is expanded by that entry of fluid under pressure, as shown in FIG. 5(b), loading the specimen 33 until a fracture occurs therein. As the pressure within the inflated pressure bag 28 is equal to the pressure within the pressure chamber 18, the load exerted on the specimen 33 is equal to that pressure sensed by the pressure transducer 21, whose operation has been explained earlier herein.

As mentioned earlier herein, dependent upon how machine 10 is utilized, it may be desirable to stiffen the machine's operations. Such stiffening of the machine could, in part, be accomplished by substitution of a piezoresistive wire pressure gauge, one such gauge being shown and described later herein in relationship to the second embodiment of the fracture loading machine 40. Such piezoresistive wire pressure gauge would be sealed within pressure chamber 18 eliminating thereby fluid volume changes therein attributable to the pressure transducer 21. Further, as will also be described with respect to fracture specimen loading machine 40, an insert, preferably of metal having a high elastic modulus can be installed in pressure bag 28 for taking up part of the volume therein. Of course, to minimize compression changes in the fluid effecting thereby the stiff characteristics of the machine, a fluid having a high bulk modulus should be selected, and the surface area of seals used in pressure chamber 18 need to be restricted to the minimum.

Pressurization of the fluid 18a in machine 10, of course, causes a heat rise, with that rise being later dissipated as the fluid temperature equalizes the temperature of the rest of the pressurizing system. Such generated heat changes in a constant volume setting causes pressure changes that can have an undesirable effect.

A second embodiment of a fracture specimen loading machine 40 is shown in FIG. 6, hereinafter referred to as machine 40. The machine 40 is like the described machine 10 but includes also: a gear train 41, driven by turning of a threaded rod 42, the gear train, turning appropriately a potientometer 43. Operation of that potientometer provides data for computing the volume of fluid within a pressure bag 44. Gear train 41 also operates screw gears 64a and 64b that open and close appropriately hinged portions of a frame 46 wherein pressure bag 44 is maintained.

Like machine 10, machine 40 consists of a housing 47 that is like housing 11, and is connected on its one end 47a to frame 46 and has threaded rod 42 turned into a longitudinal bore 48 of machine 40, and also incorporates vent 48a to atmosphere and has a pressure chamber 49 formed therein. Secured to the end of threaded rod 42, like threaded rod 13, is a piston 50. Piston 50 is arranged and functions like piston 17, and has arranged on its end 50a a gasket or O-ring seal 51 that is maintained thereto by a screw 52. Unlike machine 10, machine 40 also has a second longitudinal bore 53 formed therethrough wherein a gear train connector shaft 54 is journaled.

Threaded rod 42, like the described threaded rod 13, has a handle 55 secured across its external end 42a, below which handle, and above the threaded portion of the rod, is arranged a gear 56, whose function will be explained with respect to operations of gear train 41.

Another distinction between machine 10 and machine 40 involves the type of pressure sensor 57 preferably used in the embodiment of machine 40. As has been outlined earlier herein relating to providing very "stiff" machine operations, it is desirable to minimize volume changes in the pressure chamber 49 attributable to the pressure sensor. To this end, machine 40 preferably employs a length of piezoresistive wire installed within the fluid 18a in pressure chamber 49, that is electrically connected by wires 59a and 59b to an appropriate meter, or the like, not shown. As the piezoresistive wire 58 is immersed in that fluid its operation causes no change in fluid volume, with changes in fluid pressure being sensed as changes in resistance. Further, to "stiffen" machine operations, gasket or O-ring seal 51, like O-ring seal 19, is preferably formed from a material that will be minimally deformed when subjected to pressure, and its surface area exposed to fluid 18a is minimized.

One or more pressure bag inflation tubes 59, identical in construction and operation to inflation tube 27, are connected to pressure chamber 49 to pass fluid therefrom into pressure bag 44. Pressure bag 44 should be taken as being like the described pressure bag 28 in construction and operation, being formed from a single sheet of metal 44a, preferably stainless steel, that is folded into an envelope sandwiching a horseshoe gasket 44b therebetween, as has already been described herein. Except that, as shown in FIG. 8, it may contain a thin piece of metal 60, which metal should have a higher bulk modulus than does the fluid 18a, the use of which thin piece of metal 60, as has been discussed herein relative to machine 10, is intended to take up part of the volume within the pressure bag, limiting as much as possible the fluid therein to further "stiffen" operations of machine 40.

Also, as shown best in FIG. 8, the introduction of fluid, under pressure, into a pressure bag 44, like pressure bag 28, will cause an inflation thereof to fracture at 62 a slotted specimen 61. Machine 40, however, provides movable frame sections 46a and 46b of frame 46 that open as specimen 61 is loaded, expanding with the pressure bag, as shown best in FIG. 8, to minimize pressure bag crimping at 63, an example of which crimping is shown in FIG. 5(b) at 35.

Shown in FIG. 8, the movable portions of the frame sections are allowed to open as the pressure bag 44 is inflated by appropriate operations of screw gears 64a and 64b. Screw gears 64a and 64b are secured across the ends of screws 65a and 65b, which screws are turned through threaded holes 66a and 66b formed in the frame 46. Connected to the ends opposite to screw ends 65a and 65b opposite to screw gears 64a and 64b are plates 67a and 67b whose lower surfaces 68a and 68b contact shoulders 69a and 69b, FIGS. 7 and 8, formed on top surface of rear and side movable frame portions 70a, 70b, 71a, 71b, 72a and 72b. Plates 67a and 67b are moved away from shoulders 69a and 69b by appropriate turning of screw gears 64a and 64b, that allow plates 67a and 67b and the rear and side movable frame portions to rise in response to the inflation of pressure bag 44, precluding crimping of the pressure bag at 63. As the two movable frame sections 46a and 46b are identical, the description of one 46a should be taken as a description of the other also.

To pressure bag crimping along the sides of specimen 61, as shown best in FIG. 7, the left and right side movable frame portions 71a and 72a are provided along with rear movable frame portion 70a butting against the ends thereof at 70d and 70c. These rear and side movable frame portions are slanted upwardly along pressure bag engagement surfaces, which upward slant of rear movable frame portion is shown as to the rear movable frame portion 70a at 63a in FIG. 8. Upward pivoting of the movable frame portions 70a, 71a and 72a takes place around the rear most edges 70c, 71c and 72c of the pressure bag 44 engagement faces. As shoulders 69a of the rear and side movable frame portions 70a, 71a and 72b all butt against the lower surface 68a of plate 67a, when screw 65a is elevated the plate 67a will be allowed to rise as pressure bag 44 expands allowing also the rear and side movable frame portions 70a, 71a and 72 to pivot upward around their rear most edges 70c, 71c and 72. Such upward pivoting of the rear movable frame portion 70a is shown in FIG. 8, with upward movement of the side movable frame portions 71a and 72a, it is to be understood, while not shown, taking place along the side of the specimen 61.

As explained hereinabove, appropriate turning of screw gears 64a and 64b allows outward movement of the movable frame sections 46a and 46b. Gear train 41 is arranged to provide the desired turning of screw gears 64a and 64b, which turning is synchronized to the inflation of the pressure bag 44. Shown in FIG. 6, gear train 41 consists of drive gear 56, that is arranged on rod 42 that meshes with a connector gear 75. The body 75a of the connector gear 75 is releasably secured to an end 54a of shaft 54. Shaft 54, as has already been mentioned herein, is journaled through longitudinal opening 53, exiting through housing end 47a, and has its end installed in a collar 76 having two set screws 77a and 77b arranged therein. One set screw 77a is arranged to secure, when turned appropriately, the collar 76 to the shaft 54. A second shaft 78, hereinafter referred to as frame shaft 78, has its end fitted into collar 76. The respective ends of shaft 54 and frame shaft 78 butt into one another. Collar 76 can be locked to frame shaft 78 by appropriate turning of set screw 77b. In operation, handle 55 can be manually turned, forcing piston 50 into pressure chamber 49 pressurizing the fluid therein forcing it, ultimately, into pressure bag 44. By appropriately turning either set screw 77a or 77b, loosening it, the collar can be left unsecured, shaft 54 thereby being allowed to "free-wheel". When the pressure bag 44 has inflated to a snug fit within the slot of sample 61, before a load is applied thereto, the set screws 77a and/or 77b can be turned so as to lock the collar to the shafts. Thereafter, further turning of handle 55 turns also collar 76 and second shaft 78 to turn also potientometer 43 that is connected, by turning set screw 43a, to the end of frame shaft 78 opposite to collar 76. Turning potientometer, of course, changes the resistance across wires 43b and 43c, which change in resistance is sensed by an appropriate meter, or the like, not shown. From the reading of which meter can be calculated the volume of fluid in pressure bag 44, which fluid volume relates directly to the specimen slot opening.

Additional to connecting to collar 76 and potientometer 43, frame shaft 78 has frame drive gears 79a and 79b secured thereto by set screws 80a and 80b in meshing engagement with screw gears 64a and 64b, turning those gears appropriately, when frame shaft 78 is turned.

While an arrangement of two frame sections 46a and 46b, each having movable portions therewith, has been shown herein to be preferred, it should be obvious that only one such frame section could be so employed to minimize crimping of one surface of pressure bag 44, which utilization of only one such frame section would not depart from the subject matter coming within the present disclosure. Obviously, from the disclosure relating to machine 10, it is not required to incorporate movable frame sections as part of the present invention.

Gear train 41 shown herein as a preferred arrangement for providing synchronized movement of the movable frame portions in conjunction with the inflation of pressure bag 44. To provide such synchronized movement it is, of course, necessary to provide a gear ratio of the rod drive gear 56 to connector gear 75 and frame drive gears 79a and 79b to screw gears 64a and 64b, respectively, that will produce a desired opening of the movable frame portions in relation to the expansion of pressure bag 44. Of course, it can be assumed that a number of gear combinations and ratios would provide this desired synchronization so, while no specific ratios are mentioned herein, it should be understood that the present invention teaches utilizing such gear ratios to produce the desired synchronization. Also, while gear train 41 is shown as a preferred arrangement for operating screw gears 64a and 64b, certainly other arrangements, such as a servo operated electrically energized arrangement, not shown, or the like, could be employed to produce the desired synchronized movement.

Although a particular arrangement of movable frame sections 46a and 46b is shown herein as being preferred, it should be understood that other arrangements could be employed without departing from the subject matter coming within this disclosure. Further, while both machines 10 and 40 are shown as being manually operated, it should be obvious that rods 13 and 42 could be motor driven, or the like, without departing from the subject matter coming within this disclosure.

Although preferred embodiments of my invention in a fracture specimen loading machine have been herein disclosed, it should be understood that the present disclosure is made by way of example and that variations are possible without departing from the subject matter coming within the scope of the following claims, which subject matter I regard as my invention.

I claim:

1. A fracture specimen loading machine comprising, a source of fluid under pressure;
   fluid transfer means connected to said source of fluid under pressure for receiving fluid therefrom;
   envelope-shaped pressure bag means connected to said fluid transfer means to receive fluid therefrom, to expand as the fluid volume therein increases;
   flow control means for controlling the volume of fluid within said pressure bag; and
   sensor means connected to said fracture specimen loading machine for sensing fluid pressure within said pressure bag.

2. A fracture specimen loading machine as recited in claim 1, wherein the source of fluid under pressure consists of,
   a housing wherein is arranged a pressure chamber containing the fluid; and
   piston means fitted to travel within said pressure chamber for pressurizing said fluid and for controlling the flow of fluid into the pressure bag.

3. A fracture specimen loading machine as recited in claim 2, wherein
   the pressure chamber is part of a longitudinal bore formed in the housing, which bore has threads formed in one end with the other end thereof being smooth walled and constituting said pressure chamber; and
   a fitting, maintaining the fluid transfer means, is secured to the pressure chamber.

4. A fracture specimen loading machine as recited in claim 3, wherein the piston means consists of,
   a rod that is smooth along part thereof and is fitted to travel in the pressure chamber, having threads arranged on another part thereof to mesh with the threads formed in the bore of said housing; and
   seal means connected to the rod smooth portion for engaging the pressure chamber wall to prohibit fluid from the pressure chamber from flowing along the rod smooth portion.

5. A fracture specimen loading machine as recited in claim 4, wherein the means for moving said piston means within said pressure chamber consists of,
   a handle secured across the rod above the threaded portions thereof, extending above said housing, such that turning of said handle turns also said rod.

6. A fracture specimen loading machine as recited in claim 4, further including,
   drive means arranged with the means for moving said piston means, for providing synchronized turning of a shaft;
   sensor means releasably connected to said shaft for measuring the number of turns thereof; and means for releasably connecting said sensor means to said shaft.

7. A fracture specimen loading machine as recited in claim 6, wherein the drive means is a gear train consisting of,
   a drive gear secured to turn with the means for moving said piston means;
   a shaft journaled in the housing; and
   a gear secured to said shaft in meshing engagement with and turned by said drive gear.

8. A fracture specimen loading machine as recited in claim 6, wherein the sensor means consists of,
   a potientometer.

9. A fracture specimen loading machine as recited in claim 1, further including,
   means for measuring the volume of fluid entering the pressure bag.

10. A fracture specimen loading machine as recited in claim 1, wherein the fluid transfer means consists of,
    a stainless steel tube having an inside diameter from 0.002 to 0.003 inches and an outside diameter from 0.009 to 0.011 inches.

11. A fracture specimen loading machine as recited in claim 1, wherein the fluid is a fluid having a high bulk modulus.

12. A fracture specimen loading machine as recited in claim 1, wherein the pressure bag consists of,
    a flat sheet of thin gauge metal;
    a gasket over which said flat sheet of thin gauge material is folded into an envelope, said gasket having the inflation tube fitted therethrough and into the envelope formed by so folding said sheet of thin gauge material; and
    means for clamping said envelope along the open sides and end against said gasket therein providing a plastic flow of said gasket to seal said envelope sides and end.

13. A fracture specimen loading machine as recited in claim 12, wherein the flat sheet of thin gauge material is stainless steel; and
    the gasket is formed from copper in a U-shape.

14. A fracture specimen loading machine as recited in claim 12, further including,
    a flat plate of metal installed within the envelope formed by folding the flat sheet of thin gauge material over the gasket.

15. A fracture specimen loading machine as recited in claim 12, wherein the means for clamping said envelope consists of,
    a frame formed in a U-shape having two halves that can be secured together to sandwich the envelope of the flat sheet of thin gauge material and gasket therebetween, so as to cause a plastic flow of said gasket to seal said envelope open sides and ends, said envelope extending across the open portion of said U.

16. A fracture specimen loading machine as recited in claim 15, further including
    one of the U-shaped frame sections incorporates upward pivoting side and rear portions arranged around the interior of said U that are capable of moving with the pressure bag as it inflates;

drive means arranged with the means for moving said piston means, for providing synchronized movement of said side and rear portions in conjunction with pressure bag inflation; and means for releasably securing said drive means to said means for moving said piston means.

17. A fracture specimen loading machine as recited in claim 16, the drive means consists of, a gear train composed of:
  a drive gear secured to turn with the means for moving said piston means;
  a shaft journaled to the housing;
  a gear secured to said shaft in meshing engagement with and turned by said drive gear;
  a frame drive gear arranged with said shaft;
  means for releasably securing together said shaft and frame drive gear;
  a screw gear secured across a top end of a screw that is turned into an appropriate threaded hole formed in one of the U-shaped frame sections, said screw gear being in meshing engagement with and turned by said frame drive gear; and
a plate arranged over and in contact with the upward pivoting side and rear portions of the U-shaped frame section.

18. A fracture specimen loading machine as recited in claim 17, further including, incorporating upward pivoting side and rear portions in both U-shaped frame sections:

a second frame drive gear arranged with the shaft;
a means for releasably securing the second frame gear to said shaft;
a second screw gear secured across a top end of the screw that is turned into an appropriate threaded hole formed in the other U-shaped frame sections, said second screw gear being in meshing engagement with and threaded by said second frame drive gear; and
a second plate arranged over and in contact with the upward pivoting side and rear portions of the second U-shaped frame section.

19. A fracture specimen loading machine as recited in claim 1, wherein the sensor means consists of, a pressure transducer arranged with the fracture loading machine so as to sense pressure within the pressure bag, capable of electrically transmitting data concerned with said sensed pressure; and display means for receiving from said pressure transducer, said data reflecting the pressure within the pressure chamber for displaying said pressure.

20. A fracture specimen loading machine as recited in claim 19, wherein the pressure transducer consists of, a flexible diaphram arranged to be flexed back and forth within a body portion thereof responsive to the fluid pressure within the pressure chamber, the position of said diaphram within said body portion being electrically measured to reflect the pressure within said pressure chamber.

21. A fracture specimen loading machine as recited in claim 19, wherein the pressure transducer consists of, a piezoresistive wire sealed within the pressure chamber, said piezoresistive wire when subjected to a change in fluid pressure, suffers a change in electrical resistivity.

* * * * *